US011391675B2

United States Patent
Poutanen et al.

(10) Patent No.: US 11,391,675 B2
(45) Date of Patent: Jul. 19, 2022

(54) OPTICAL SENSOR FOR HYDROGEN BONDING GASEOUS MOLECULES

(71) Applicant: Tampere University Foundation sr, Tampereen yliopisto (FI)

(72) Inventors: Mikko Poutanen, Luoma (FI); Arri Priimägi, Somero (FI); Olli Ikkala, Helsinki (FI)

(73) Assignee: Tampere University Foundation sr, Tampereen yliopisto (FI)

( * ) Notice: Subject to any disclaimer, the term of this patent is extended or adjusted under 35 U.S.C. 154(b) by 50 days.

(21) Appl. No.: 16/639,330

(22) PCT Filed: Aug. 31, 2018

(86) PCT No.: PCT/FI2018/050617
§ 371 (c)(1),
(2) Date: Feb. 14, 2020

(87) PCT Pub. No.: WO2019/043297
PCT Pub. Date: Mar. 7, 2019

(65) Prior Publication Data
US 2020/0217802 A1   Jul. 9, 2020

(30) Foreign Application Priority Data

Aug. 31, 2017   (FI) .................................. 20175784

(51) Int. Cl.
*G01N 21/77* (2006.01)
*G01N 21/81* (2006.01)
(Continued)

(52) U.S. Cl.
CPC ........... *G01N 21/77* (2013.01); *C07C 245/08* (2013.01); *C08L 39/08* (2013.01); *G01N 31/222* (2013.01);
(Continued)

(58) Field of Classification Search
CPC ................. G01N 21/77; G01N 31/222; G01N 2021/758; G01N 2021/7769;
(Continued)

(56) References Cited

U.S. PATENT DOCUMENTS 5,319,975 A   6/1994   Pederson et al.
5,599,913 A   2/1997   Harris et al.
(Continued)

FOREIGN PATENT DOCUMENTS

CN   106566564 A   4/2017
CN   107011317 B   3/2020
(Continued)

OTHER PUBLICATIONS

Kojima, M. et al. "Effect of solvent on cis-to-trans isomerization of 4-hydroxyazobenzene aggregated through intermolecular hydrogen bonds," J. Phys. Org. Chem. 2005; 18: 994-1000 (Year: 2005).*
(Continued)

*Primary Examiner* — Jennifer Wecker
*Assistant Examiner* — Michelle Adams
(74) *Attorney, Agent, or Firm* — Ziegler IP Law Group, LLC

(57) ABSTRACT

An optically transparent matrix including a molecule containing a hydroxyazobenzene group or its derivative embedded in the matrix. An optical system including the optically transparent matrix, an isomerizing light source, and one or more light detector(s) for measuring absorbance changes from the optically transparent matrix. A method for measuring the quantity of hydrogen bonding gaseous molecules.

35 Claims, 8 Drawing Sheets

(51) Int. Cl.
*G01N 31/22* (2006.01)
*C07C 245/08* (2006.01)
*C08L 39/08* (2006.01)
*G01N 21/75* (2006.01)

(52) U.S. Cl.
CPC ............. *G01N 2021/758* (2013.01); *G01N 2021/7769* (2013.01); *G01N 2201/122* (2013.01)

(58) Field of Classification Search
CPC .. G01N 2201/122; G01N 21/33; G01N 21/81; C07C 245/08; C08K 5/23
See application file for complete search history.

(56) References Cited

U.S. PATENT DOCUMENTS

| | | | |
|---|---|---|---|
| 2002/0148948 | A1 | 10/2002 | Hensel |
| 2003/0211618 | A1 | 11/2003 | Patel |
| 2012/0309904 | A1 | 12/2012 | Xu et al. |
| 2015/0050743 | A1 | 2/2015 | Horváth et al. |
| 2016/0299083 | A1 | 10/2016 | Martinez et al. |
| 2016/0327529 | A1 | 11/2016 | Kim |
| 2017/0044373 | A1 | 2/2017 | Gu et al. |
| 2017/0090251 | A1 | 3/2017 | Mizusaki et al. |

FOREIGN PATENT DOCUMENTS

| | | |
|---|---|---|
| JP | 2006275817 A | 10/2006 |
| JP | 2006282990 A | 10/2006 |
| JP | 2007197609 A | 8/2007 |

OTHER PUBLICATIONS

Riyad, Y.M. et al. "Optical switching of azophenol derivatives in solution and in polymer thin films: The role of chemical substitution and environment," American Journal of Nano Research and Application 2014; 2(6-1): 39-52 (Year: 2014).*

European Patent Office, Extended European Search Report, Application No. 18850872.5, dated Apr. 9, 2021, 10 pages.

Garcia-Amoros Juame et al, "Understanding the fast thermal isomerisation of azophenols in glassy and liquid-crystalline polymers", Physical Chemistry Chemical Physics, vol. 16, No. 7, p. 3108, XP055787522, ISSN: 1463-9076, DOI: 10.1039/c3cp54519a, Jan. 1, 2014, 7 pages.

Ryabchun, Crown-Ether and Azobenzene-Containing Liquid Crystalline Polymers: An Influence of Macromolecular Architecture on Optical Properties and Photo-Orientation Processes, wileyonlinelibrary.com/journaujpola, Dec. 8, 2010.

McCarrick et al. Assessment of a Chromogenic Calix[4]arene for the Rapid Colorimetric Detection of Trimethylamine, Mater. Chem., 1994, 4(2), 217-221.

Poutanen et al. Thermal Isomerization of Hydroxyazobenzenes as a Platform for Vapor Sensing, ACS Macro Lett 2018, 7, 381-386.

International Search Report, Patent Cooperation Treaty, Application No. PCT/FI2018/050617, dated Dec. 7, 2018, 5 Pages.

Patent Cooperation Treaty, (Second) Written Opinion of the International Preliminary Examining Authority, Application No. PCT/FI2018/050617, dated Oct. 7, 2019, 9 Pages.

Patent Cooperation Treaty, (First) Written Opinion of the International Searching Authority, Application No. PCT/FI2018/050617, dated Dec. 7, 2018, 9 Pages.

Patent Cooperation Treaty, International Preliminary Report on Patentability, Application No. PCT/FI2018/050617, dated Dec. 17, 2019, 23 Pages (Includes Applicant's Response to Written Opinion of Jun. 19, 2019 with amended claim set).

Lv et al., "Reactive Azobenzene Liquid-Crystalline Block Copolymer as a Promising Material for Practical Application of Light-driven Soft Actuators", Journal of Materials Chemistry C, vol. 3:26, DOI: 10.1039/C5TC00595G, Published May 29, 2015, 8 pages.

Weis et al., "Visible-Light-Responsive Azopolymers with inhibited π-π Stacking Enable Fully Reversible Photopatterning", ACS Publications, Macromolecules, vol. 49:17, DOI: 10.1021/acs.macromoL6b01367, 2016, 6 pages.

Yin et al., "Theoretical Study of the Trans—cis Isomerization Mechanism of Azobenzene Substituents in Rhenium complexes". Abstracts of the 30th Annual Meeting of The Chinese Chemical Society, Chapter 18: Development and Application of Electronic Structure Theory and Method, 1 page.

National Intellectual Property Administration, P.R. China, First Office Action, dated Feb. 10, 2022, 10 pages.

* cited by examiner

OPTICAL SENSOR FOR HYDROGEN BONDING GASEOUS MOLECULES

FIELD OF THE APPLICATION

The present application relates to an optically transparent matrix, to an optical system comprising the optically transparent matrix, and to methods and uses for measuring the quantity of hydrogen bonding gaseous molecules. The present application also relates to sensors and methods for measuring humidity and temperature.

BACKGROUND

Humidity sensors are used to measure the humidity in air, often as a fraction of the maximum amount of water that can be absorbed by air at a certain temperature. Under normal atmospheric conditions and at a given temperature, this fraction can vary between 0 and 100%. This relative humidity (RH) measurement is only valid under the above-mentioned temperature and atmospheric conditions, thus making very important the fact that the sensor must not be affected by temperature or pressure changes. However, as the relative humidity is a function of both temperature and absolute moisture content, small temperature variations translate into relative humidity variations, and therefore the sensors have usually integrated temperature sensors.

Humidity and moisture sensors are used in monitoring humidity contents for example in gases, and other materials like oil and soil. They are also used in monitoring air quality, drying processes, humidors etc. On an industrial level, humidity sensors are used widely in controlling humidity and moisture levels to improve yields and ensure safety and quality in various production facilities. Facilities that need controlled environments during process operations include for example diverse chemical plants, pharmaceutical and semiconductor industries. These processes also often challenge the capabilities of the sensors as the environments can have harsh conditions or other gases, requiring highly stable and selective sensors.

The dominant humidity-sensing technologies in the market are based on permittivity changes in a polymer matrix induced by water adsorption from air, resulting in changes in capacitance or conductivity. These approaches have been well established, but they are not suitable for all environments and many of the humidity sensors are subject to drift so they need regular recalibration. In addition, these technologies need clean room processes during manufacturing and in these technologies, the electronics need to be integrated into the probe, which poses a challenge for several environments where remote sensing would be the preferred, or in some cases the only, option. As a measurement parameter, conductivity is a property of the manufactured sensor chip, and therefore it is also susceptible to errors due to variations in manufacturing and accurate sensors need chip specific calibration.

SUMMARY

The present application provides a detection scheme for measuring relative humidity and/or other hydrogen-bonding gases from the environment, in combination with temperature measurement, by following the thermal cis-trans isomerization kinetics of hydroxyazobenzene derivatives embedded into an optically transparent matrix, which acts as the active sensing layer. To have the material in a state where it isomerizes thermally, it is illuminated periodically with light with wavelength capable of inducing trans-cis isomerization. The thermal isomerization kinetics of the cis-trans isomerization of such a material is sensitive to the presence of hydrogen-bonding molecules, which adsorb to the active sensing layer from the measurement environment. In the case of water, the thermal isomerization kinetics has an exponential dependence on the relative humidity. The thermal isomerization kinetics is also sensitive to the measurement temperature. The isomerization is followed by measuring absorbance changes optically. The absorbance can be followed with a single or multiple wavelengths. Combinations of different hydroxyazobenzene derivatives and sensing wavelengths allows for simultaneous measurement of temperature and multiple gases with a single sensor layer. The optical measurement of the absorbance changes can be implemented in various ways, for example by embedding the measurement into a sensing system based on optical fibers.

The present approach offers a simple solution with low-cost materials where it is possible to measure both temperature and relative humidity optically from a single sensing layer. It is also possible to distinguish the presence of other hydrogen-bonding gases with the sensor. The measured parameter, i.e. isomerization speed, is a material property, and thus is not dependent on the exact device geometry. Owing to this, there is no need for device specific calibration as there is in the conventional humidity sensors. In addition, the lack of need for calibration allows also for easy replacement of the sensing parts in case they have been worn out.

The present application provides an optically transparent matrix comprising a molecule containing a hydroxyazobenzene group or its derivative embedded in the matrix.

The present application also provides an optical system comprising
  the optically transparent matrix,
  an isomerizing light source, and
  means for measuring absorbance changes from the optically transparent matrix.

The present application also provides a method for measuring the quantity of hydrogen bonding gaseous molecules, the method comprising
  providing the optically transparent matrix or the optical system,
  illuminating the optically transparent matrix with isomerizing light capable of inducing trans-cis isomerization in the hydroxyazobenzene group or its derivative,
  measuring absorbance changes from the optically transparent matrix at a single or multiple wavelength(s) to obtain thermal cis-trans isomerization time constant, and
  obtaining the quantity of the hydrogen bonding gaseous molecules by using the dependency of the thermal cis-trans isomerization time constant to the quantity of the hydrogen bonding gaseous molecules.

The present application also provides use of the optically transparent matrix or the optical system for measuring humidity, temperature and/or hydrogen bonding gaseous molecules.

The main embodiments are characterized in the independent claims. Various embodiments are disclosed in the dependent claims. The embodiments recited in dependent claims and in the description are mutually freely combinable unless otherwise explicitly stated.

The embodiments utilize photoswitchable azobenzene compounds. Azobenzene molecules undergo photoisomerization from a thermally stable trans-state to a metastable cis-state upon photon absorption. The reverse reaction can be driven with light of another wavelength, while it can also occur thermally. The wavelengths that trigger the isomerization reactions, as well as the thermal lifetime of the cis-isomer, are dictated by the substitution pattern of the molecule. Importantly, the isomerization reaction gives rise to significant changes in the absorption spectrum of the azobenzene, rendering it relatively straightforward to monitor the isomerization dynamics in real time. This, combined with the fact that the isomerization dynamics is highly environment-dependent, provides the basis for the present humidity-sensing concept.

The detection scheme is based on measuring the thermal isomerization kinetics by monitoring the absorbance changes in thin films of hydroxyazobenzene derivatives embedded into a polymer matrix. In such material, water as well as other hydrogen-bonding gases provide a catalytic effect on the thermal isomerization, making the isomerization dynamics highly sensitive to for example relative humidity and allowing for fast sensing with large dynamic range and high accuracy. Experiments have revealed that the lifetime of the cis isomer scales exponentially as a function of relative humidity, and changes by up to two orders of magnitude have been recorded.

The azobenzene molecules and their kinetics provide a highly tunable measurement scheme in which the measurement is easy to implement and as the measured quantity is speed, it is easy to measure accurately. Combined with the large changes in the isomerization speed provided by the catalytic activity of adsorbed water molecules, it is possible to obtain very accurate sensing of relative humidity. In addition to the dependence on relative humidity, the sensor has a significant temperature dependence, but importantly, owing to the large range of possibilities provided by the different azobenzene molecules, with their combinations, it is possible to distinguish the effects from relative humidity and temperature and therefore simultaneously measure them both with the single sensor.

It is also possible to solve the issue of distinguishing the effect of changes in temperature and humidity by introducing another azobenzene molecule, and measuring both simultaneously.

Since the humidity sensor solution is optically controlled, it can be managed from a distance. That will bring many advantages for example for satellites, weather balloons, and in hazardous environments, such as ones involving radio-activity, high magnetic fields or electromagnetic interference. In addition, the expansion of usage of Internet-of-Things (IoT) devices drives the need for more and more remotely-controlled sensors. Remotely-controlled IoT humidity sensor for example for agriculture purposes brings huge possibilities for improved accuracies in weather analysis for farming.

Adoption of humidity and moisture sensors is increasing for instance due to the increased safety that monitoring ensures, in both process and discrete applications. Monitoring also helps in increasing yield in chemical and petrochemical industry sectors. In addition, control of moisture levels in fuel gases and fuel oils helps ensure required combustion value.

Accuracy of all meteorological measurement systems is important. For example. weather predictions affect our lives via food production and agriculture, logistics (maritime and air traffic), and also our free time. The changing climate and extreme weather conditions require better weather predictions, and hence also improved accuracy in analysing and measuring the current weather conditions. Being able to control humidity content in pharma and food and beverage products can extend their lifetimes, thereby bringing benefits to society at large in terms of reduced waste. The sensors disclosed herein may be applied to these fields of technology as well.

DETAILED DESCRIPTION

Figure 1:
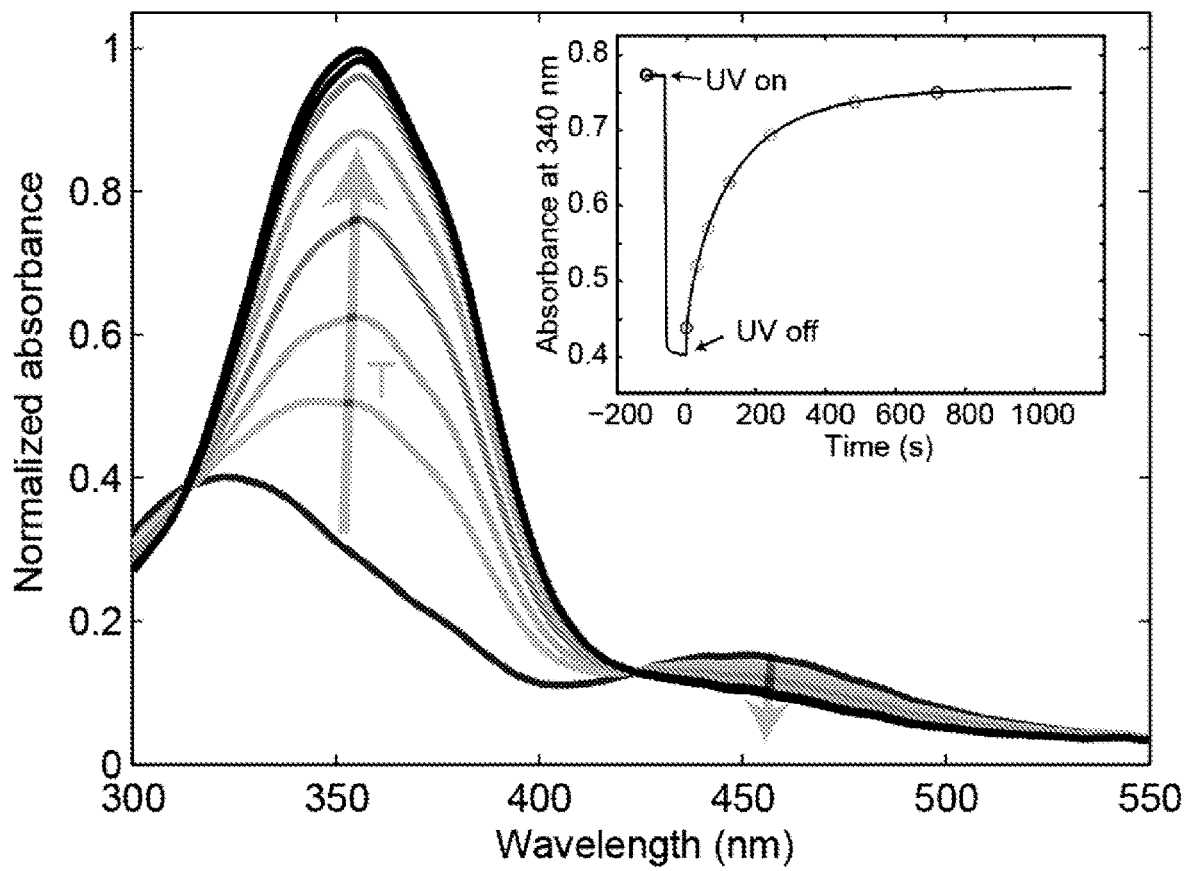
FIG. 1 shows an example of the spectral changes upon isomerization from which the isomerization kinetics are measured. The inset shows an example of the isomerization kinetics as followed with a single wavelength measurement.
Figure 2:
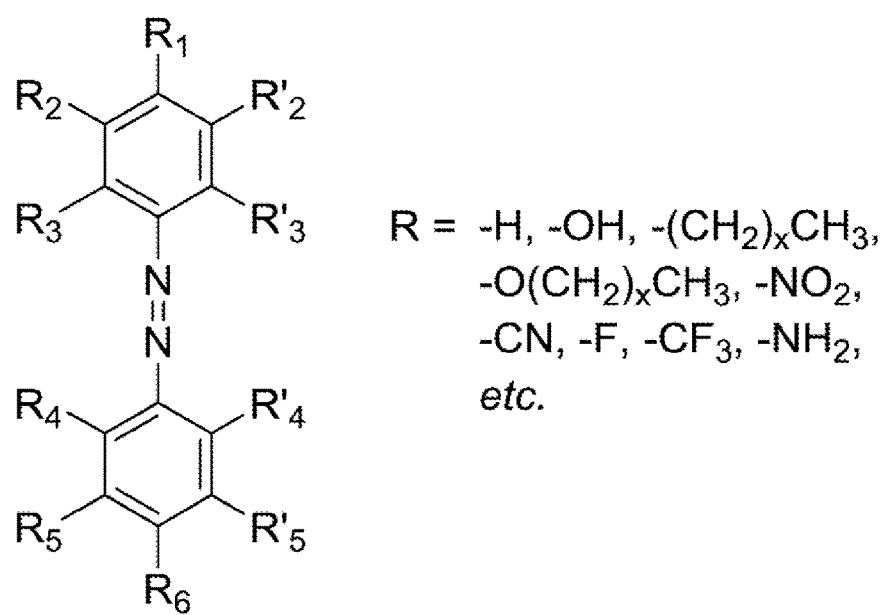
FIG. 2 shows a group of hydroxyazobenzene molecules, which are highly sensitive to the environmental conditions, with examples of the possible substituting groups to which the disclosed detection scheme can be applied. The molecule should contain at least a single —OH group. In the sensor, the active measurement layer can be a combination of different molecules of the environmentally highly sensitive hydroxyazobenzene molecules or then the hydroxyazobenzene molecules can be combined with other types of isomerizing or thermochromic molecules.
Figure 4:
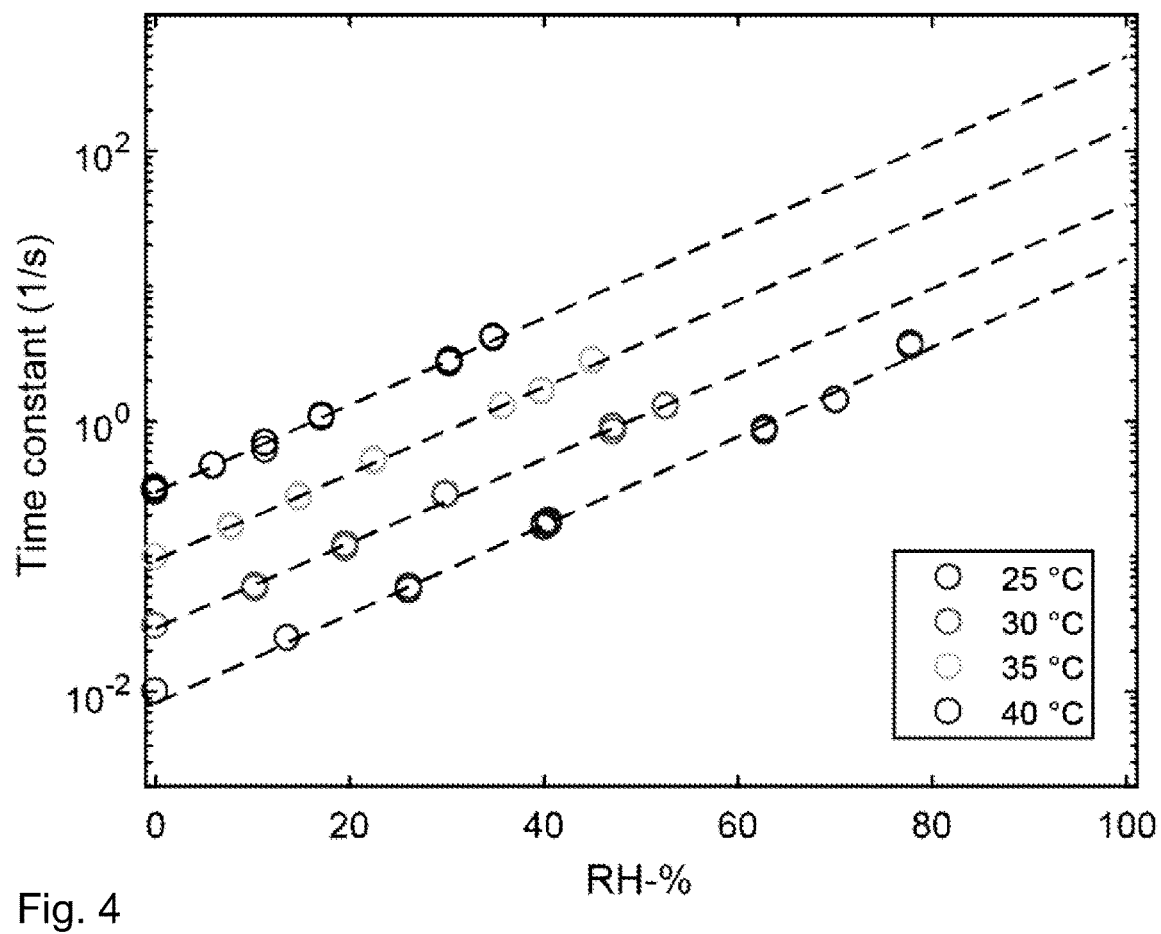
FIG. 4 shows an example of the dependence of the time constant, k, of the thermal cis-trans isomerization with respect to relative humidity.
Figure 5:
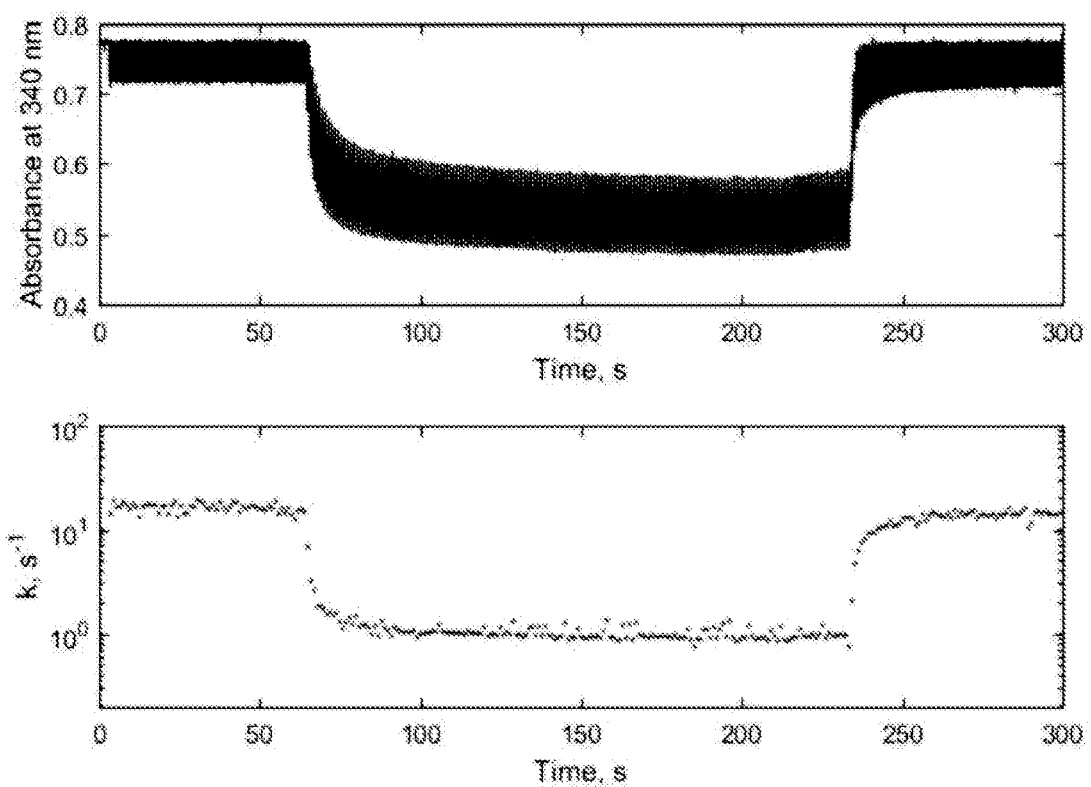
FIG. 5 shows the response time of the films is on the scale of seconds. Top) An example of the measured absorbance changes from a sample illuminated periodically with 365 nm UV light upon relative humidity change from 80% to 0% and back. The absorbance changes of single isomerization cycles are not visible. Bottom) The isomerization time constants, k, of the exponential change of the absorbance as extracted from the isomerization cycles. The time constants vary exponentially with respect to relative humidity.

The detection scheme for measuring relative humidity and/or other hydrogen bonding gases in combination with temperature is based on following the thermal cis-trans isomerization kinetics by monitoring the absorbance changes (see FIG. 1) in active sensing layers containing hydroxyazobenzene derivatives (see FIG. 2 for exemplary chemical structures) embedded into an optically transparent matrix. In such a material, water as well as other hydrogen-bonding gases like methanol, ethanol, acetic acid etc. provide a catalytic effect on the thermal isomerization through hydrogen-bond-assisted tautomerization (see FIG. 3) making the isomerization dynamics sensitive to the presence of hydrogen-bonding gaseous molecules in the measurement environment. The molecules adsorb into the sensing layer depending on their quantity in the gaseous environment, which allows for sensing of the hydrogen-bonding gases in the environment. The response of the thermal isomerization time constant is exponential as a function of relative humidity as shown in FIG. 4. To create a sensor, the isomerization constants are extracted from isomerization cycles (see FIG. 5), and from these, the relative humidity values are extracted based on calibration curves similar to FIG. 4. The upmost line represents the highest temperature 40° C., and the lowest line represents the lowest temperature 25° C.

The active sensing layer is a thin film, with a thickness varying from nanometers to a few micrometers and contains the hydroxyazobenzene molecules. The active sensing layer can be produced with various solution deposition techniques such as spin coating, dipping or drop casting from a solution to which the matrix material and the hydroxyazobenzene derivatives have been dissolved/dispersed. The starting material can also be a polymerizable compound, which can be polymerized to create the sensing layer. In case of other than polymeric matrix material, other deposition methods, like vapor deposition techniques, can be used. The thickness of the sensing layer is varied to optimize the response time and measurement of the spectral changes. The sensing layer can also be a part of a layer structure for example with gas selective layers or protective layers.

The active sensing layer is an optically transparent matrix comprising a molecule containing a hydroxyazobenzene group or its derivative embedded in the matrix. The molecule containing a hydroxyazobenzene group or its derivative may be called as active molecule. The products, entities, devices and the like containing said transparent matrix comprising a molecule containing a hydroxyazobenzene group or its derivative embedded in the matrix may be called in general as sensors. Embedding as used herein refers to including or integrating a compound into a matrix, which may act as a carrier or support. The compound may be embedded throughout the matrix or it may be embedded partially, such as on the surface or predominantly on the surface of the matrix. This may depend on the manufacturing method. For example if the compound is mixed with matrix material before forming the final structure, the compound would be evenly distributed. On the other hand, if the compound is applied onto a previously formed matrix, it may not be evenly distributed but may stay mainly at the surface area of the matrix.

The matrix may comprise a polymer, more particularly one or more polymer(s), such as organic polymer(s), or the matrix is based on said polymer(s). The organic polymer may be a plastic polymer, such as thermoplastic or thermosetting polymer. These polymers may provide required transparency and enable embedding the active molecules. It was found out that polyvinyl polymers are suitable materials for the matrix for attaching and embedding the hydroxyazobenzene group molecules to the matrix and for obtaining desired optical and functional properties, such as permeability, hygroscopicity, formability, transparency etc. Especially polymers comprising poly(4-vinyl pyridine) were found suitable. In one embodiment matrix comprises poly(4-vinyl pyridine). The matrix is preferably hygroscopic, for example in order to allow water to penetrate it. The active sensing layer may also be present as a coating on a substrate, such as glass, quartz or plastic, for example in a form of a sheet, plate or the like. The active sensing layer may also be present as a coating at an end of an optical fiber. The matrix is present as solid, such as a solid layer or coating. Preferably the matrix does not contain hydrogen bond donors. The matrix itself is at least partially or substantially transparent.

Figure 3:
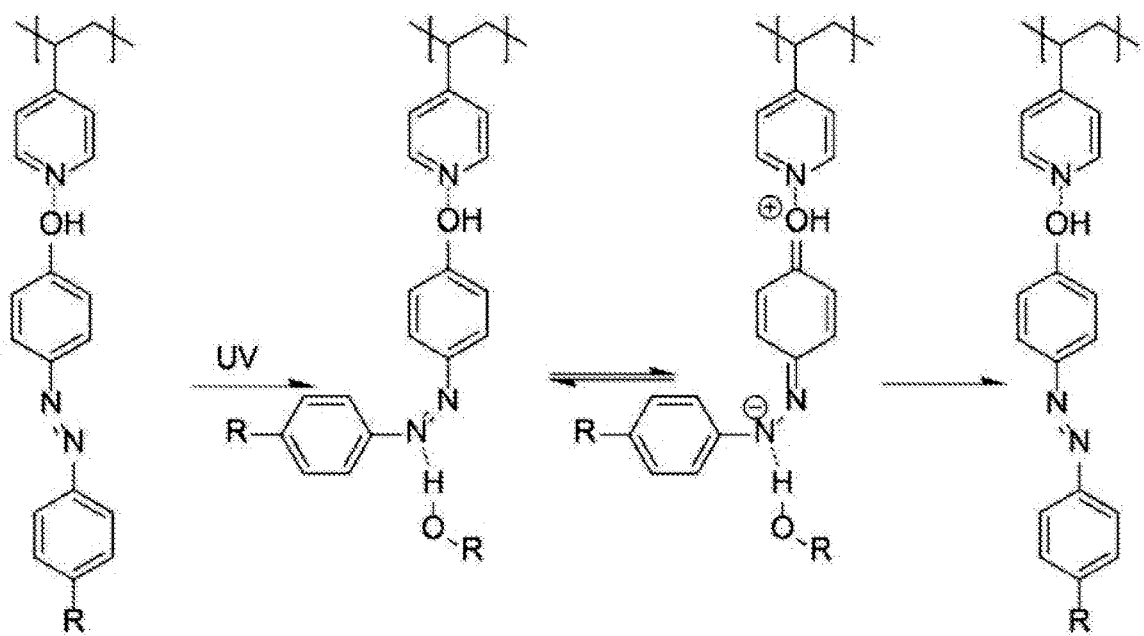
FIG. 3 shows how hydrogen-bonding induces tautomerization of the —OH group, which enables the rotational pathway for the cis-trans isomerization. The cis-trans isomerization through the rotational pathway is significantly faster than through the inversional pathway, which is favored without the hydrogen bonding.

In one embodiment the hydroxyazobenzene group or its derivative is hydrogen bonded to the matrix, as seen in the example of FIG. 3.

In one embodiment the hydroxyazobenzene group or its derivative is part of a larger molecule or a polymer, so it may be covalently bonded to the matrix. The hydroxyazobenzene group or derivative thereof may be reacted with the larger molecule or the polymer to form a covalent bond.

The optically transparent matrix may have a thickness from nanometers to a few micrometers, such as from 5 nm to 20 μm, for example in the range of 5-5000 nm, 10-3000 nm, 100-2000 nm, or 500-2000 nm. In one example the optically transparent matrix has a thickness of about 1 μm.

In one embodiment the optically transparent matrix further comprises a second molecule containing a hydroxyazobenzene group or its derivative embedded in the matrix. The first and the second molecule containing a hydroxyazobenzene group or its derivative may have different properties, such as different isomerization wavelengths, isomerization kinetics, absorption spectra or combinations thereof. This way it is possible to obtain more accurate measurements and monitor more parameters compared to using one type of active molecule.

In one embodiment the optically transparent matrix further comprises another isomerizing or thermochromic molecule embedded in the matrix. Also this may enable obtaining more accurate measurements and monitoring more parameters.

The matrix may comprise 5-100 mol %, for example 5-50 mol % 5-20 mol %, or 5-10 mol %, or 10-100 mol %, 20-100 mol % or 50-100 mol % of the active molecules, such as molecules containing a hydroxyazobenzene group or its derivative or other isomerizing or thermochromic molecules. Most measurements were done with 100 mol %, i.e. one active molecule per each polymer repeat unit. Therefore in one example the matrix comprises 90-100 mol % of the active molecules. The matrix may consist of the molecules disclosed herein, such as the matrix polymer(s) and the molecule(s) containing a hydroxyazobenzene group or its derivative, or it may further contain other molecules in trace amounts only, such as less than 1 mol %, less than 0.5 mol % or less than 0.1 mol %, or less than 1% (w/w), less than 0.5% (w/w) or less than 0.1% (w/w).

Figure 6:
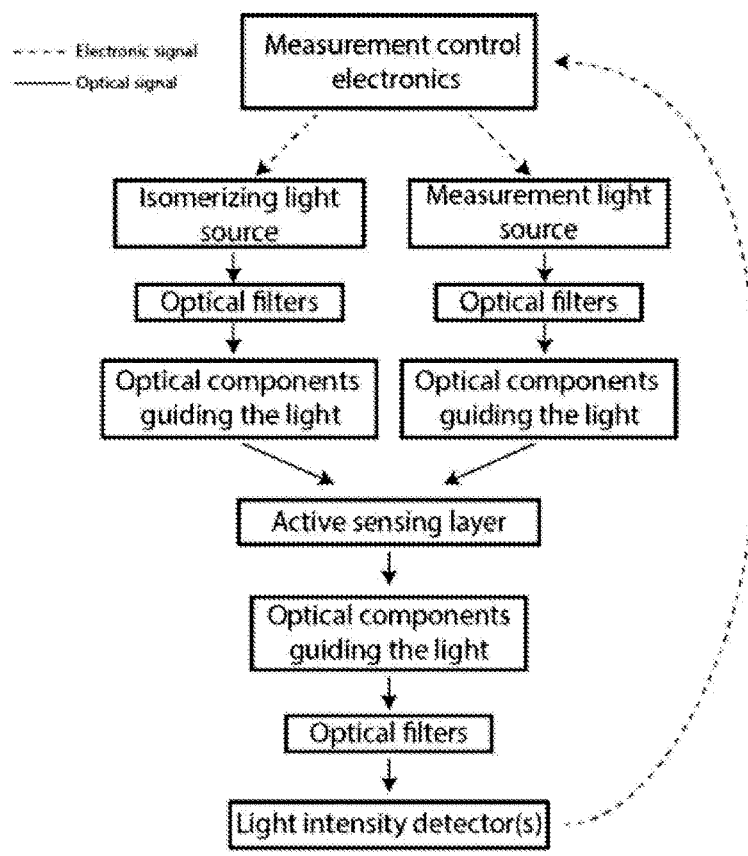
FIG. 6 shows a schematic description of the measurement setup.

The thermal isomerization kinetics is followed by measuring the changes in the absorbance of the active layer of the sensor as a function of time. A schematic presentation of the possible measurement system is described in FIG. 6. To have the sample in a condition in which thermal isomerization is occurring, the sample is illuminated in a controlled manner with an isomerizing light source, which has the wavelength usually in the ultra violet range. The light source can be an LED, laser or any other source providing the required wavelength and intensity. The isomerizing light can be also guided to the sensing layer from a remote light source with various optical components. The illumination is controlled electronically to achieve optimal conditions for the measurement. The absorbance changes are measured using either single or multiple wavelengths at which the used molecule or their combination has absorbance changes. A second light source can be used for the measurement light, but the light source can be also the same as for the isomerizing light. The spectral bandwidth of the used light source can be controlled with band-pass filters before the light is guided to the sample and optionally before the measurement of the light intensity, band-pass filters can be used to separate the isomerization light wavelength from the absorbance measurement wavelength. The isomerizing light and the measurement light can also be of the same wavelength.

The isomerizing molecules, which provide the basis for the measurement, are embedded into optically transparent polymer matrix such as poly(4-vinyl pyridine) (P4VP), but the possible matrices are not limited to P4VP or to polymers as such. The possible matrices are such that they are optically transparent, allow the trans-cis isomerization of hydroxyazobenzenes, adsorb the measured molecules from environment and do not have significant amounts of hydrogen bond donating groups so that they would affect the sensing of the hydrogen-bonding molecules.

The molecules that can be used in the described detection scheme contain a hydroxyazobenzene group or its derivative. The hydroxyazobenzene moiety can contain one or more hydroxyl groups. Also otherwise, the chemical substitution pattern of the used hydroxyazobenzene can be varied significantly. All of the other positions in the hydroxyazobenzene molecule can be chemically substituted (see FIG. 2) or the hydroxyazobenzene derivative can be part of a larger molecule or as a part of a polymer. Varying the chemical substitution patterns is used for tuning the sensitivity, and spectral and isomerization properties of the active layer and thereby the properties of the sensing device.

The molecule containing a hydroxyazobenzene group or its derivative, which may be called as hydroxyazobenzene molecule, acts as an active molecule, more particularly as a photoswitchable and/or photochromic compound, which reacts to the hydrogen-bonding gases and/or temperature. The properties of the molecules of this group were found advantageous to be used in the applications disclosed herein. The molecules are sensitive to the measured agents, react fast and allow accurate measurement of the reaction. The molecules can also be easily attached and/or embedded to the matrix materials, and they remain and function well in the matrix.

The molecule containing a hydroxyazobenzene group or its derivative may be 4-hydroxyazobenzene. The molecule containing a hydroxyazobenzene group or its derivative may be fluorinated.

In one embodiment the molecule containing a hydroxyazobenzene group or its derivative comprises the hydroxyazobenzene of Formula (I):

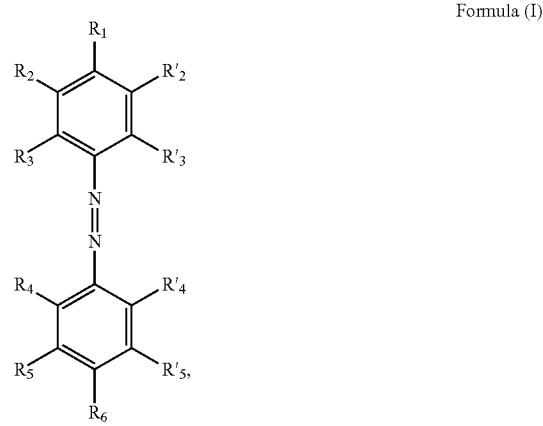

Formula (I)

wherein R is selected from —H, —OH, —$(CH_2)_xCH_3$, —$O(CH_2)_xCH_3$, —$NO_2$, —CN, —F, $CF_3$ and —$NH_2$.

In one embodiment the molecule containing a hydroxyazobenzene group or its derivative is 4-octyl-4'-hydroxyazobenzene. In one embodiment the molecule containing a hydroxyazobenzene group or its derivative is 4-ethyl-4'-hydroxyazobenzene. In one embodiment the optically transparent matrix comprises 4-(4-ethylphenylazo)phenol (2PAP) embedded into a poly(4-vinylpyridine) (P4VP) matrix.

Figure 7:
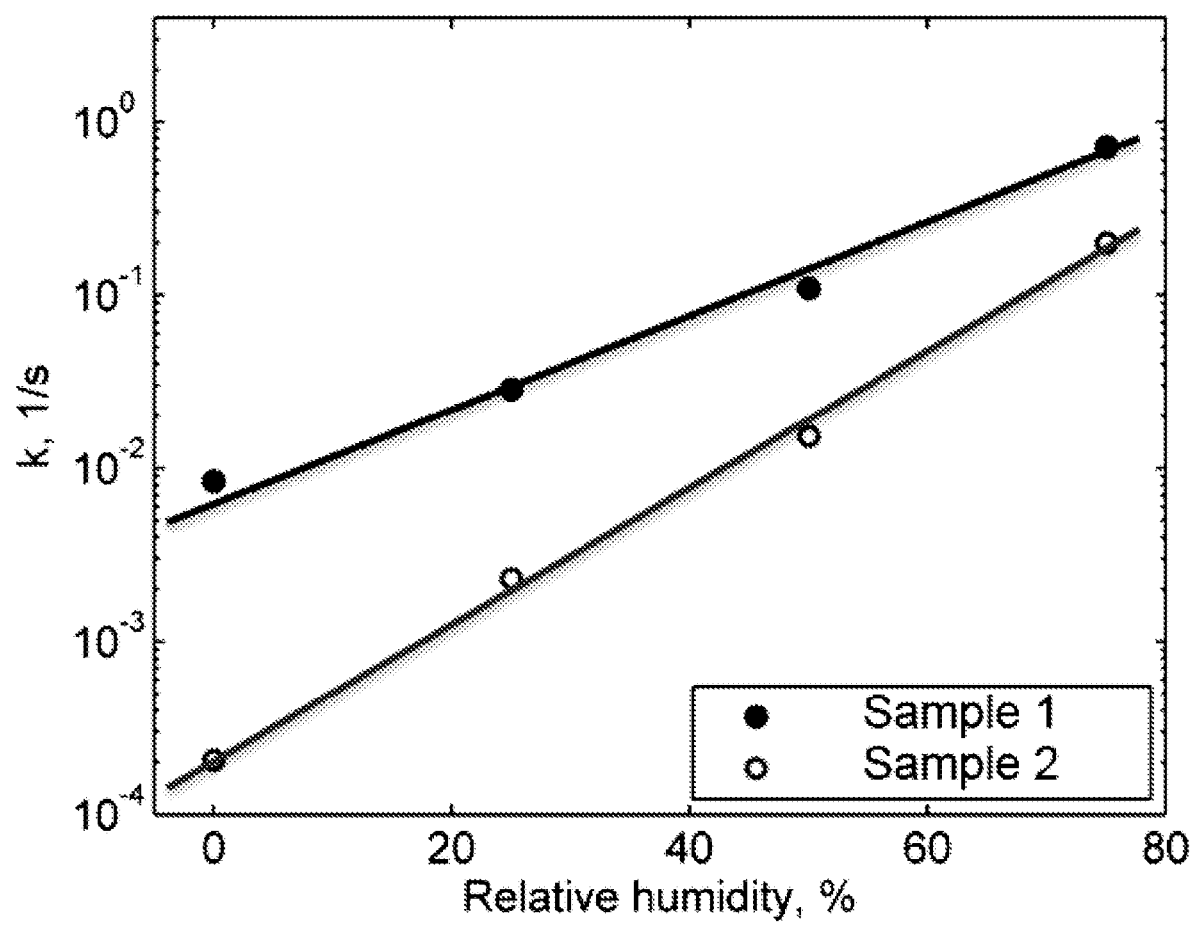
FIG. 7 shows an example of the different sensitivities of different molecules in the same matrix. Here, the hydroxyazobenzene derivative in Sample 1 (the upper line) is 4-octyl-4'-hydroxyazobenzene and Sample 2 (the lower line) is 4-ethyl-4'-hydroxyazobenzene, and the molecules are embedded into poly(4-vinyl pyridine) matrix.

Embedding multiple derivatives of the hydroxyazobenzene molecules into the same matrix allows for distinguishing the effects from relative humidity, temperature and the presence of other hydrogen bonding gases. This is made possible by the different sensitivity of the molecules used and their different spectral properties. An example of the different responses of two rather similar molecules are shown in FIG. 7. The differences in the spectral properties of the derivatives allow for distinguishing the isomerization of the different derivatives. In addition to the hydroxyazobenzene derivatives, the sensing layer can be embedded for example with other isomerizing or thermochromic molecules to improve the distinguishing of the effects of temperature and other gases.

The optically transparent matrix described herein may be used in an optical system, such as a sensing system or sensor system, for example a sensor device. The optical system may comprise the optically transparent matrix, an isomerizing light source, and means for measuring absorbance changes from the optically transparent matrix.

In one embodiment the means for measuring absorbance changes comprise one or more light detector(s), such as light intensity detector(s). A light detector may be called as photodetector or photosensor. Examples of light detectors include photodiodes and photo transistors.

In one embodiment the means for measuring absorbance changes are arranged to measure at a single or multiple wavelength(s). The wavelength(s) may be at UV and/or visible range, such as in the range of 280-700 nm, for example 280-400 nm or 315-400 nm for UV light and/or 400-700 nm for visible light.

In one embodiment the optical system comprises a second light source as a measurement light. In such case the isomerizing light source can be considered as a first light source.

In one embodiment the light source is selected from a LED and a laser. This applies both to the isomerizing light source and to the second light source. The light source may provide light at a wavelength in the ultra violet range and/or in the visible range, such as in the range of 280-700 nm, for example 280-400 nm or 315-400 nm for UV light and/or 400-700 nm for visible light, which may be the wavelength(s) capable of isomerizing the hydroxyazobenzene molecule. The light source may be combined with one or more optical filter(s), which pass only light with desired wavelength(s). The light source may be also combined with one or more optical component(s) guiding the light, such as light guide(s) and/or optical fiber(s).

In one embodiment the optical system comprises measurement control electronics arranged to control the isomerizing light source, the means for measuring absorbance changes, and optionally the second light source. The measurement control electronics may include one or more control unit(s) comprising one or more processor(s), memory, and software arranged to carry out the controlling and/or calculating actions to carry out the method(s) described herein. The one or more control unit(s) may be for example arranged to calculate the quantity of hydrogen bonding gaseous molecules, for example based on the detected absorbance changes in the optically transparent matrix by using the dependency of the thermal cis-trans isomerization time constant to the quantity of the hydrogen bonding gaseous molecules. A result is obtained from the calculation(s), which result may be provided as an output, such as a numerical value in a display or the like, or the output may be forwarded to a data system, such as a computer or embedded system or the like, which will store the outputted value(s). The outputted value(s) may be further utilized, for example used as input for a control system which is arranged as a response to the inputted value(s) to carry out one or more controlling actions using one or more actuators or other devices which may change the state of the environment, for example by changing temperature, a state of a valve, a fan, or the like. Such response aims to keep one or more parameters or other values at a desired range. It is also possible to fire an alarm as a response to the outputted value(s), if a predetermined limit value is reached.

The one or more control unit(s) may be also functionally connected to the light source(s) and arranged to control the light source(s), for example by switching a light source on and off to obtain desired illumination of the optically transparent matrix, and/or functionally connected to the means for measuring absorbance changes from the optically transparent matrix and arranged to control the means for measuring absorbance changes from the optically transparent matrix, such as a light detector, to obtain measurement value(s) and to use the values for the calculations to obtain a result. An example of such an arrangement is presented in FIG. 6, which shows electronic signal (dotted lines) and optical signal (solid lines) pathways in the arrangement.

In one embodiment the optical system comprises means for obtaining the quantity of hydrogen bonding gaseous molecules by using the dependency of the thermal cis-trans isomerization time constant to the quantity of the hydrogen bonding gas molecules, preferably based on one or more calibration curve(s).

In one embodiment the optical system comprises one or more optical fiber(s). The optical fiber(s) may be used to conduct light. This enables placing the optically transparent matrix, or a sensor comprising thereof, to a different location from the light source(s) and detector(s). The sensor may be integrated with the optical fiber(s), for example the sensing layer may be as a coating at an end of an optical fiber. This is useful for example when it is not desired to expose the electronics and components to the measuring conditions, for example due to high magnetic fields, chemicals or other harmful conditions. The matrix containing the hydroxyazobenzene molecule can tolerate such conditions.

With the described scheme for sensing, it is possible to measure relative humidity, temperature and hydrogen-bonding gases with an optical system in which the electronics can be separated from the sensing environment. The optical system can be integrated for example into a system based on optical fibers.

The aspects of the disclosed embodiments can be used for measuring relative humidity, temperature and hydrogen-bonding gases from the environment. The sensor can be designed to measure one or more of the aforementioned quantities.

The system can be implemented as a standalone sensor or it can be integrated into existing systems.

By optimizing the properties of the polymer matrix and by for example employing fluorinated hydroxyazobenzenes, the sensitivity can be tuned. The fluorination is anticipated also increase the photostability, allowing devices driven with visible light.

By using several photoactive dyes with different absorption spectra, it is possible to provide a dual-sensor, which may be used for cross-sensitivity.

The device design can be made such that the whole sensor is integrated into a compact fiber-optic device setup.

In case there would be variations of measurement accuracy of isomerization kinetics within the measurement range, the thermal isomerization speed can be enhanced by plasticising the polymer matrix.

The products described herein may be used in methods for detecting quantity of hydrogen bonding gaseous molecules, such as water, methanol, ethanol, or acetic acid, and/or for measuring humidity and/or temperature. For example water is detected in humidity measurements.

The method may comprise providing the optically transparent matrix or the optical system described herein. The optically transparent matrix or the optical system, which may be in a form of a sensor, is provided to an environment which is to be monitored. The sensor or the optically transparent matrix or the optical system may be remotely controlled, and may be wired and/or connected with one or more optical fibers.

The environment may be any suitable environment wherein monitoring of the substances or parameters mentioned herein is desired. For example, the environment may be every day environment, especially in the case of monitoring humidity and/or temperature, such as outdoor environment or indoor environment, such as a house or other building. The environment may be open or closed environment. The environment may be industrial environment or facility, for example production facility, plant, storage, or the like. The sensor may be embedded into substances such as oil, water, solvent or the like, so the environment may also be a liquid environment comprising one or more of said substances.

Examples of industries include agricultural, food, beverage, chemical, pharmaceutical, high voltage engineering and semiconductor industries. The sensor described herein may be placed for example in a container, room, hall, chamber, machinery or the like in the industry or other environment, especially involving hazardous or otherwise challenging conditions, such as strong magnetic and/or electrical fields, harmful chemicals, radiation and the like. Especially the present sensors may be applied in conditions and environments wherein the use of conventional sensors is challenging.

The method comprises illuminating the optically transparent matrix with isomerizing light capable of inducing trans-cis isomerization in the hydroxyazobenzene group or its derivative. More particularly the optically transparent matrix is illuminated with isomerizing light with wavelength capable of inducing trans-cis isomerization. Such wavelength may be in the range of 280-700 nm, for example 280-500 nm or 315-400 nm for UV light, such as in the range of 330-460 nm or 340-450 nm, for example at about 340 nm, 395 nm and/or 450 nm, and/or at visible range, such as in the range of 400-700 nm. The matrix may be illuminated at one or more wavelength(s). The illumination may be provided as one or more pulse(s).

After illuminating, absorbance changes from the optically transparent matrix at a single or multiple wavelength(s) are measured to obtain thermal cis-trans isomerization time constant.

Finally the method comprises obtaining the quantity of the hydrogen bonding gaseous molecules by using the dependency of the thermal cis-trans isomerization time constant to the quantity of the hydrogen bonding gaseous molecules.

"Trans-cis isomerization" refers to isomerization of a molecule from trans form into cis form. Correspondingly, "cis-trans isomerization" refers to isomerization of a molecule from cis form into trans form.

In one embodiment the hydrogen bonding gaseous molecules are being adsorbed into the optically transparent matrix. The matrix should be at least partially hygroscopic and/or permeable to said molecules to allow this.

The method may be a method for measuring humidity. The method may also be a method for measuring temperature. Both the humidity and the temperature may be measured. Any of the matrixes, systems or arrangements disclosed herein may be used in said methods.

EXAMPLES

In the examples it is demonstrated that thin polymer films containing hydroxyazobenzenes offer a conceptually novel platform for sensing hydrogen-bonding vapors in the environment. The concept is based on accelerating the thermal cis-trans isomerization rate through hydrogen-bond-catalyzed changes in the thermal isomerization pathway, which allows for devising a relative humidity sensor with high sensitivity and quick response to relative humidity changes. The approach is also applicable for detecting other hydrogen-bonding vapors such as methanol and ethanol. Employing isomerization kinetics of azobenzenes for vapor sensing opens new intriguing possibilities for using azobenzene molecules in the future.

Azobenzenes are a particularly versatile class of photoswitchable compounds, as they exhibit two isomeric states, trans and cis, with a large difference in geometry, absorption spectra, and dipole moment. The power of azobenzenes lies in the fact that the lifetime of the metastable cis-isomer can be controlled over a wide range, from milliseconds in push-pull azobenzenes up to even several months in ortho-substituted azobenzenes. While fast thermal relaxation is useful in, for example, optical switching and the long-lived cis-state desired in photobiology, azobenzene derivatives whose thermal isomerization dynamics depends strongly on the environmental conditions are particularly interesting. As the most prominent example, 4-hydroxyazobenzenes can experience a change of up to 5 orders of magnitude in the cis-lifetime in nonpolar versus polar solvents due to hydrogen-bond-assisted tautomerization.

Figure 8:
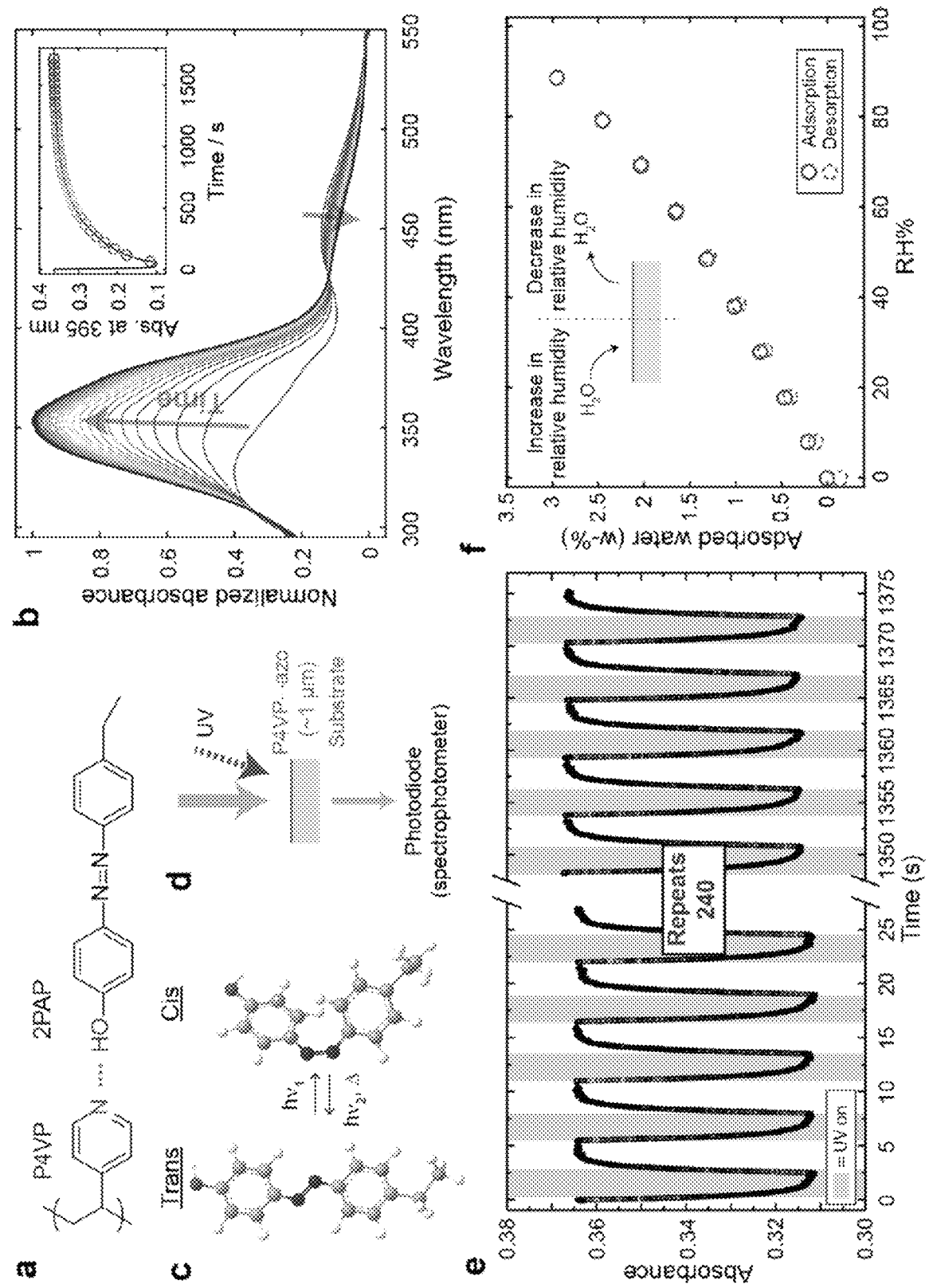
FIG. 8 shows (a) Supramolecular, nominally stoichiometric complex of poly(4-vinylpyridine) (P4VP) and 4-(4-ethylphenylazo)phenol (2PAP). (b) Spectral changes of a thin film of nominally equimolar P4VP(2PAP) complex after UV irradiation. Inset: thermal cis-trans relaxation of the same sample. (c) Trans- and cis-isomers of 2PAP. (d) Simplified schematic representation of the experimental geometry. The gray and blue arrows indicate white probe light and UV pump light, respectively. (e) An example of the reproducibility of the thermal isomerization over 250 pumping-relaxation cycles. (f) Adsorption and desorption isotherms of water at 25° C. for the equimolar P4VP(2PAP) complex.

As depicted in FIG. 8a, 4-(4-ethylphenylazo)phenol (2PAP) was embedded into a solid poly(4-vinylpyridine) (P4VP) matrix. P4VP and 2PAP form hydrogen-bonded supramolecular complexes, allowing high 2PAP loading to be used without phase separation: thin films of P4VP(2PAP) remain amorphous and of high optical quality, even at a nominally equimolar complexation ratio, corresponding to 80 wt % azobenzene concentration. Upon UV (365 nm) irradiation, the 2PAP molecules undergo efficient trans-cis isomerization in the solid state, as illustrated by the spectral changes shown in FIG. 8b (FIG. 8c displays the trans- and cis-isomers of 2PAP). The samples are thin films (~1 μm) on glass/quartz substrates and the spectral changes are measured in transmission (FIG. 8d). The spectral changes are typical to azobenzene derivatives: the π-π* transition centered at 352 nm decreases significantly upon UV illumination, while the n-π* transition at 450 nm strengthens, indicating efficient trans-cis isomerization.

The inset of FIG. 8b displays the thermal cis-trans isomerization of the 2PAP molecules in the P4VP matrix. In liquids and in polymers above glass transition temperature ($T_g$), the thermal isomerization typically follows simple first-order kinetics. However, it turns out that a stretched exponential function, that is, Kohlrausch-Williams-Watts function (1), explains better the findings $$A(t)=(A_0-A_\infty)e^{-(kt)^\beta}+A_\infty \quad (1)$$

where $A_0$ is the absorbance after illumination, $A_\infty$ is the absorbance of the fully relaxed, that is, all-trans, state, β is the stretching exponent, and k is the rate constant of thermal isomerization. In fact, this is not surprising, as the stretched exponential function is known to explain, for example, glassy relaxations. The effect of using stretching exponential function is minimal for our results and we retain from further analysis of the stretching exponents. In our material system, the isomerization process is highly reproducible, as illustrated in FIG. 8e: no changes in isomerization dynamics were observed over 250 subsequent repeat cycles (the standard deviation of the fitted time constants was 2.7%), provided that the experimental conditions (temperature, humidity) remain unchanged. Even if the azobenzene units may eventually degrade by photo-oxidation, they show potential to withstand over at least 20000 repeat cycles without significant degradation (<5% absorbance decrease).

The vapor-sensing ability of the P4VP(2PAP) complexes is based on the slight hydrophilicity of the material. Due to this, even if both P4VP and 2PAP are insoluble in water, their complex is able to adsorb a small amount of water (or other hydrogen-bonding molecules) from the environment. As shown in FIG. 8f, the water vapor uptake is approximately 3.0 wt % at 90% RH, which translates to about 0.6 water molecules per 2PAP molecule for the equimolar complex. In general, more molecules will adsorb upon an increase in RH and vice versa. The shape of the adsorption isotherm depends on the chemical activity of the vapor species as well as the properties of the polymer material, and it is important for the sensing ability.

Figure 9:
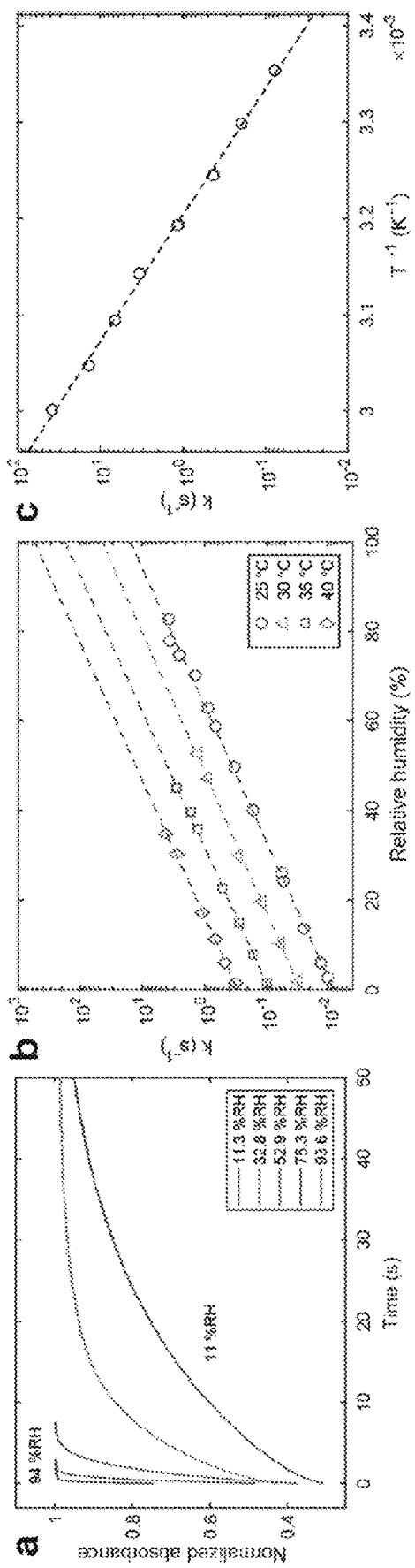
FIG. 9 shows relative-humidity dependence of thermal isomerization of a thin film of nominally equimolar P4VP(2PAP) complex. (a) Thermal isomerization curves at different RH values. (b) Rate constants of the cis-trans isomerization at different RH values at different temperatures. (c) Arrhenius-type temperature dependence of the rate constant of thermal isomerization measured at 30% RH. (d) Proposed mechanism for the sensitivity of the isomerization rate constant to the presence of hydrogen-bonding species.
Figure 9:
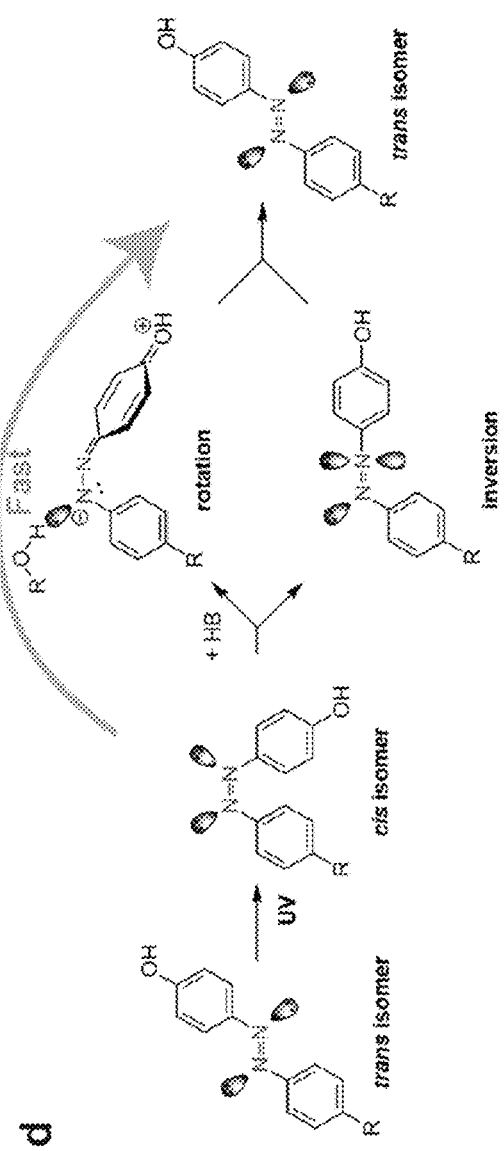

The thermal isomerization rate constant, k, shows a strong exponential dependence ($\sim e^{\lambda \cdot RH}$) on the relative humidity, RH (FIGS. 9 a,b), and the sample-related constant, $\lambda$, is $0.0755 \pm 0.0021 \%^{-1}$. The rate constants at 25° C. vary from 0.01 to 3.73 $s^{-1}$ between 2.6% and 82.7% relative humidity. The change is nearly 400-fold, and the exponential behaviour suggests the difference between 0% RH and 100% RH to be 1000-fold for the equimolar complex. This yields a huge dynamic range for the isomerization-based humidity sensor. Measurements at different temperatures reveal the Arrhenius-type ($\sim e^{-Ea/\cdot RH}$) temperature dependence (FIG. 9c) of the rate constant, with apparent energy of activation, $E_a$, of 146±7 kcal/mol. The dependence on RH is exponential at all the studied temperatures (FIG. 9b). This shows that the RH and temperature dependencies are decoupled, which is an important feature from the sensing point of view. Overall, based on the results of FIG. 9ac, the time constant can be described as $$k(T, \text{RH}) = k_0 e^{-Ea/RT} \cdot e^{\lambda \cdot RH} \quad (2)$$

where $k_0$ is a sample-dependent constant, Ea is the apparent energy of activation, R is the gas constant, and RH is the relative humidity at temperature T. It is assumed that the RH dependence arises from the water induced intrinsic changes in the isomerization pathway. The hypothesized mechanism is depicted in FIG. 9d. The two classical routes for thermal cis-trans isomerization are inversion and rotation. For an unsubstituted azobenzene molecule, inversion is favoured, while for push-pull type azobenzenes, rotation is the dominating isomerization pathway. The latter has a significantly lower activation energy, resulting in shorter lifetimes of the cis-isomer. In 4-hydroxyazobenzenes, hydrogen bonding to the —N═N— moiety by, for example, water or ethanol molecules shifts the azo-hydrazone equilibrium toward the hydrazone form, thus, effectively easing the rotational isomerization pathway. This leads to a drastic decrease in the cis-lifetimes, that is, an increase in the thermal isomerization rate constants upon increasing RH. The lack of side reactions allows the isomerization cycles to be repeated continuously and with high accuracy, which renders hydroxyazobenzenes optimal for devising a reliable, high-performance sensor for water vapor or other hydrogen-bonding vapors.

Figure 10:
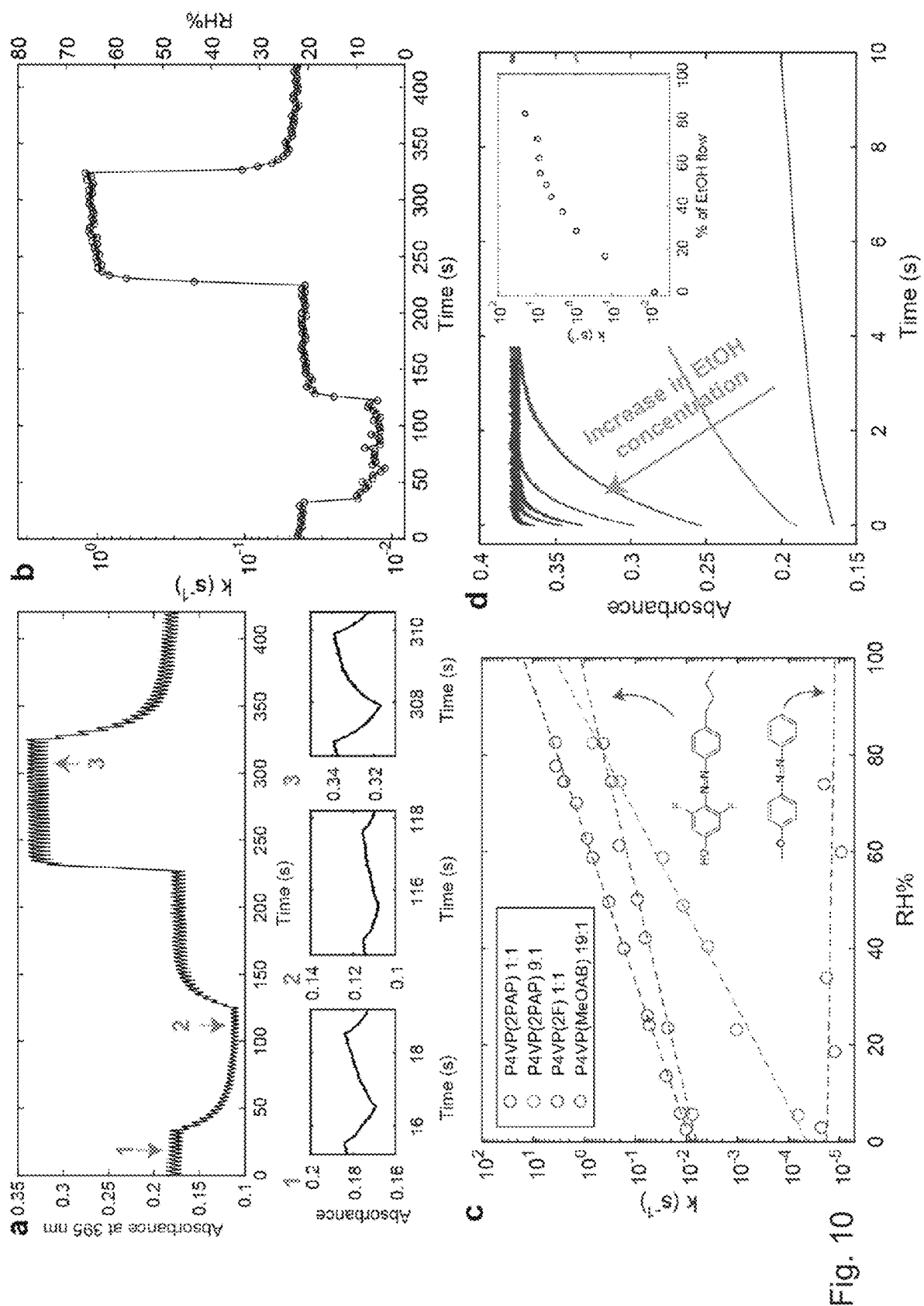
FIG. 10 shows (a) Example of the use of the isomerization kinetics as a relative humidity sensor by pulsed UV irradiation (1 s) and following the cis-trans isomerization (2 s). The insets 1-3 show examples of the partial thermal relaxations (increase in absorbance) at three different RH values (~20% RH, ~5% RH, and ~70% RH, respectively). (b) Rate constants extracted from the relaxations in (a) and the RH values obtained from equation 2 and data shown in FIG. 9. (c) RH dependencies of rate constants for different azobenzene-containing polymer systems. (d) Sensitivity of the rate constants to the presence of ethanol. The inset shows the rate constants as a function of percentage of ethanol flow ($N_2$ bubbled through ethanol).

To demonstrate the potential of the proposed method in an actual sensing device, the sample is kept constantly in a nonequilibrium state by pulsed illumination with 365 nm light, and the kinetics of the thermal isomerization is measured for each relaxation. Upon humidity transients from ~20% RH to low (~5% RH) and high humidities (~70% RH), the thermal isomerization constant changes rapidly. Based on the exponential dependence, the logarithmic scale of the rate constants is translated to linear scale of RH values (FIG. 10b).

Figure 11:
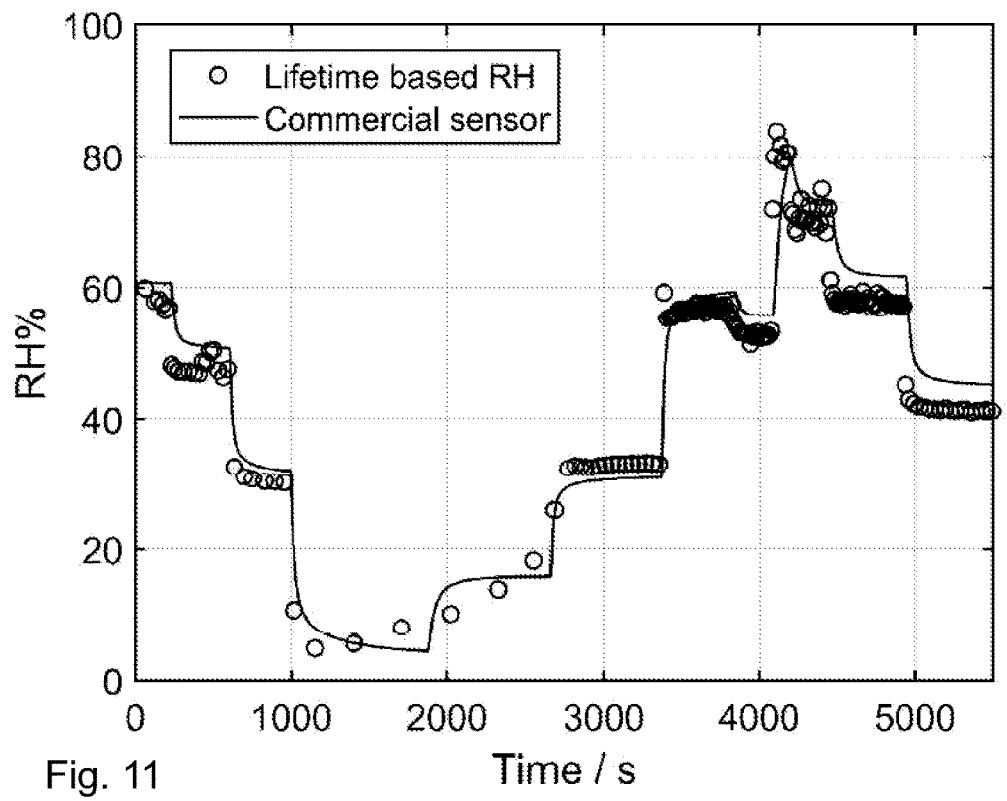
FIG. 11 shows a comparison of the isomerization rate constant based sensor to a commercial hygrometer (TESTO 635-2). The measurement is done at 23° C. and the RH is calculated based on the data in FIG. 2. The deviations are expected to arise from temperature changes on the film surface induced by the changes in the gas flow.
Figure 12:
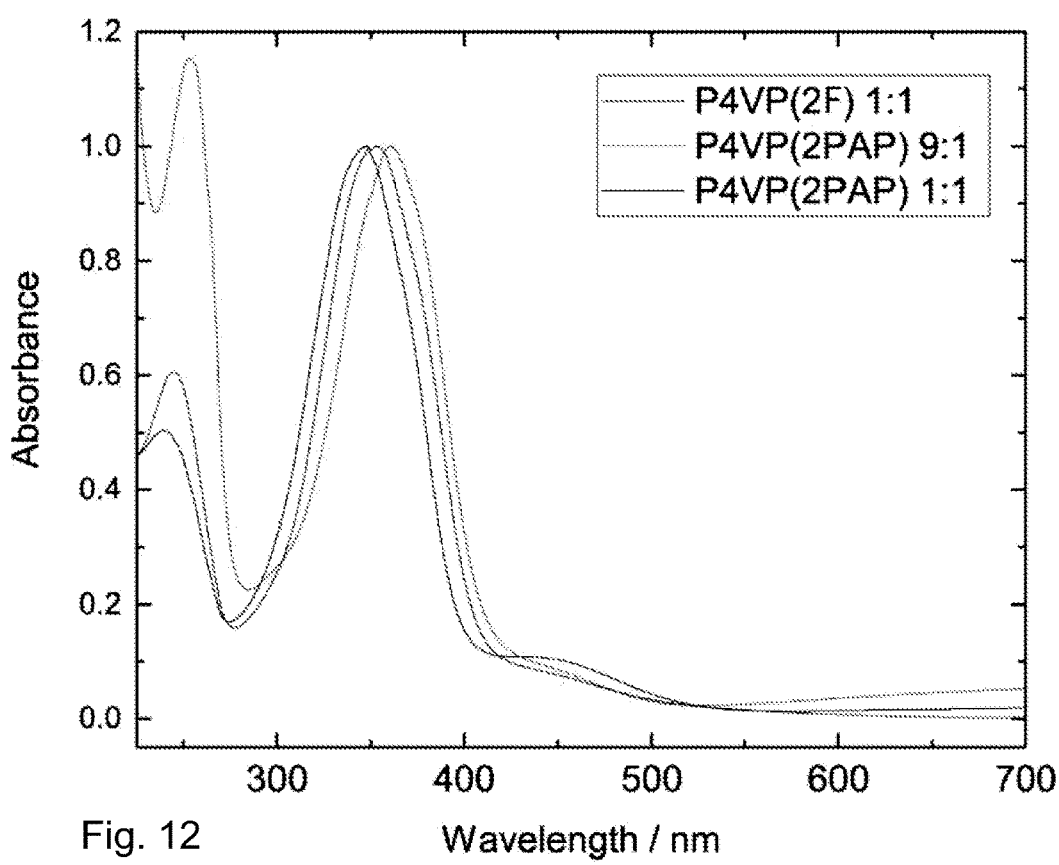
FIG. 12 shows the normalized spectra for the samples reported in FIG. 10. The absorbance maxima are 347 nm, 361 nm and 352 nm for P4VP(2F) 1:1, P4VP(2PAP) 9:1, P4VP(2PAP) 1:1, respectively.

A comparison to a commercial hygrometer is shown in FIG. 11. Upon an increase of humidity from 20% RH to 70% RH, the response time for 90% change is 11 s and upon decrease is 15 s. The response speed is a result of the fast equilibration of the adsorption of water molecules into the polymer film, arising from the use of a thin (about 1 µm) active layer.

Based on the results, the hydroxyazobenzene-based vapor sensor is fast, accurate, and reliable. It was noted that the use of hydroxyazobenzenes is critical for it to function. This is demonstrated in FIG. 10c by using 5 mol % mixtures (with respect to monomers) of 4-methoxyazobenzene (MeOAB) and P4VP. The methoxy functionality is not able to tautomerize as the hydroxy group is, and therefore, the mixture does not show any dependence on the RH. Furthermore, in higher mixing ratios, the MeOAB phase separates from the polymer, unlike the supramolecular P4VP(2PAP) complex where the phenol-pyridine hydrogen bonding allows high azobenzene concentration to be used. FIG. 10c also shows that the sensitivity of humidity detection can be optimized by changing the material composition. Using 10 mol % of 2PAP in P4VP, instead of the equimolar complexation, increases the hydrophilicity of the material system and decreases the cis-lifetime at dry conditions, leading to a dynamic range of 5 orders of magnitude. On the other hand, when 2PAP is replaced with its ortho-fluorinated counterpart, 4-((4-butylphenyl)diazenyl)-3,5-difluorophenol (2F) (inset of FIG. 10c), the material becomes more hydrophobic and the hydrogen-bond-accepting ability of the cis-azo group weakens. Both of these decrease the RH sensitivity, as is clearly evident from FIG. 10c. Overall, these results confirm the proposed mechanism, that is, that 4-hydroxyazobenzene derivatives are able to create functional sensors, the major requirement being a tautomerizable azobenzene molecule and a matrix that does not contain hydrogen-bond donors. Finally, FIG. 10d demonstrates that the sensing ability is not limited to water, but the system can detect also other hydrogen-bonding vapors, as demonstrated here using ethanol. In principle, by combining different hydroxyazobenzene molecules with distinct spectral changes into the same matrix, one can foresee the possibility of simultaneously measuring relative humidity and temperature or independently detecting several hydrogen-bonding vapors within one photoactive polymer film.

In summary, it is shown that the thermal isomerization kinetics of 4-hydroxyazobenzenes offer a robust platform for sensing hydrogen-bonding vapors. The strong dependence on the environment, that is, the high sensitivity of the device demonstrated, arises from the intrinsic changes in the isomerization pathway through tautomerization, induced by the presence of hydrogen-bond-donating molecules such as water vapor. The dependence of the thermal lifetime on relative humidity is shown to be exponential, and changes of up to 5 orders of magnitude between dry and wet conditions were observed. Importantly, the Arrhenius-type temperature dependence of thermal isomerization is decoupled from the dependence on relative humidity close to room temperature. The reproducibility of the isomerization allows using the isomerization kinetics as an optically readable vapor sensor with high accuracy. In addition to relative humidity, the sensor can detect also other hydrogen bonding vapors, as demonstrated for ethanol. The sensitivity of the device can be optimized by tuning the material composition. Importantly, the concept provides a pathway toward remote sensing of gases and vapors using fiber-optic connections and suppresses the need for device-specific calibration taken the type of the gas or vapor is known. We present here what we believe to be the first azobenzene isomerization-kinetics-based vapor sensor, yet are confident that by clever materials design, the concept can be expanded toward other types of analytes as well.

EXPERIMENTAL SECTION

Materials and Methods.

Poly(4-vinylpyridine) (Mn=1000 g/mol) was purchased from Polymer Source and solvents were purchased from Sigma-Aldrich and used as received. The 4-(4-ethylphenylazo)phenol was synthesized through azo-coupling of 4-ethylaniline and phenol according to a previously published procedure and 4-methoxyazobenzene (purity >99.0%) was purchased from Sigma-Aldrich and used as such. (E)-4-((4-butylphenyl)diazenyl)-3,5-difluorophenol was synthesized through azo-coupling of 3,5-difluorophenol and diazonium salt of butyl aniline. Thin films were prepared by dissolving poly(4-vinylpyridine) (P4VP) and the azobenzene in question into chloroform (15 mg/ml) and mixing them to obtain the desired molar ratio. The solutions were spin coated onto glass or quartz substrates with spinning conditions chosen such that the maximum absorbance of the films would be around unity. The UV-vis absorption spectra of the thin films under dark conditions were measured using Agilent Cary 5000 spectrophotometer. The spectral change upon thermal isomerization kinetics was measured using an Ocean Optics 2000+ diode array spectrometer with a deuterium halogen light source (DH-2000 BAL, Ocean Optics).

Thermal Isomerization Measurements.

The cis-lifetimes were determined by following the absorbance at a single wavelength (395 or 340 nm) by using either Agilent Cary 60 spectrophotometer or a photodiode equipped with a 10 nm bandpass filter (398 nm, OD 4, Edmund Optics). A 365 nm light-emitting diode (Thorlabs) equipped with a 10 nm bandpass filter was used to induce the trans-cis-isomerization. The intensity and duration of the illumination was controlled electronically. To avoid any unwanted isomerization, the probe beam was incident on the sample only when collecting the data and blocked otherwise. The maximum observed absorbance change at 395 nm was 70%, but the actual absorbance change is limited by the thermal rate constant (temperature, gaseous environment) and illumination intensity. Stretched exponential function (eq 1) is used for the fitting, except in cases of partial relaxations measured upon sensing, for example, FIG. 10a.

Relative Humidity Control.

The isomerization measurements were done inside a temperature and humidity-controlled chamber equipped with glass windows for transmission measurements. The temperature was controlled with a resistive heating element and a Eurotherm temperature controller. The relative humidity was controlled by combining controlled flows of dry nitrogen with a flow bubbled through water. The temperature and relative humidity in the measurement chamber was measured with TESTO 635-2 hygrometer.

Dynamic Vapor Sorption.

The water vapor adsorption of the equimolar complex P4VP(2PAP) was measured by dynamic vapor sorption equipment DVS ET (Surface Measurement Systems). The sorption cycle was 0-90% RH with 10% RH steps and desorption cycle employing a reverse sequence. The sample was measured as a drop-casted thin film on a thin glass substrate. The weight of the substrate was subtracted from the results.

Synthesis of (E)-4-((4-butylphenyl)diazenyl)-3,5-difluorophenol (2F)

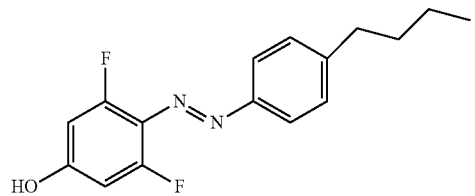 [SMILES: CCCCc1ccc(/N=N/c2c(F)cc(O)cc2F)cc1]

An aqueous solution of NaNO$_2$ (7.10 mmol, 0.49 g) was added to a precooled (0° C.) mixture of butyl aniline (6.70 mmol, 1.0 g); acetone/water (1:1, 17 ml) and concentrated HCl (1.67 ml). The resultant mixture was stirred at 0° C. for 15 minutes. In a separate flask, a mixture of 3, 5-difluorophenol (7.21 mmol, 0.938 g), NaOH (7.16 mmol, 0.286 g) and K$_2$CO$_3$ (11.18 mmol, 1.18 g) was prepared in water (17 ml) and cooled to 0° C. The diazonium salt prepared earlier was slowly added to this phenolic solution at 0° C. and the resultant mixture was allowed to stir at same temperature for another 30 minutes. The reaction mixture was diluted with ethyl acetate and the organic phase was separated, washed with water and concentrated on rotary evaporator.

The invention claimed is:

1. An optical system for obtaining a quantity of hydrogen bonding gaseous molecules, the optical system comprising
    an optically transparent matrix comprising a molecule containing a hydroxyazobenzene group embedded in the matrix;
    an isomerizing light source;
    at least one light detector for measuring absorbance changes from the optically transparent matrix; and
    measurement control electronics configured to control the isomerizing light source, the at least one light detector, and optionally a second light source, wherein the measurement control electronics are configured to
        control the isomerizing light source to illuminate the optically transparent matrix with isomerizing light capable of inducing trans-cis isomerization in the hydroxyazobenzene group,
        control the at least one light detector to measure absorbance changes from the optically transparent matrix at a single or multiple wavelength(s) to obtain a thermal cis-trans isomerization time constant, and
        obtain the quantity of the hydrogen bonding gaseous molecules by using a dependency of the thermal cis-trans isomerization time constant on the quantity of the hydrogen bonding gaseous molecules.

2. The optical system of claim 1, wherein the molecule containing a hydroxyazobenzene group comprises the hydroxyazobenzene of Formula (I):

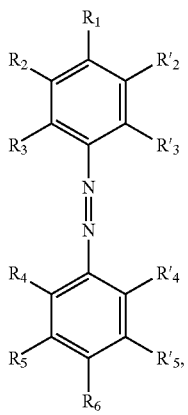

Formula (I)

wherein all $R_1$-$R'_6$ and $R'_2$-$R'_5$ are selected from —H, —OH, —(CH$_2$)$_x$CH$_3$, —O(CH$_2$)$_x$CH$_3$, —NO$_2$, —CN, —F, —CF$_3$ and —NH$_2$, wherein the hydroxyazobenzene of Formula (I) includes at least one —OH group.

3. The optical system of claim 1, wherein the molecule containing a hydroxyazobenzene group is 4-hydroxyazobenzene.

4. The optical system of claim 1, wherein the molecule containing a hydroxyazobenzene group is 4-octyl-4'-hydroxyazobenzene.

5. The optical system of claim 1, wherein the molecule containing a hydroxyazobenzene group is 4-ethyl-4'-hydroxyazobenzene.

6. The optical system of claim 1, wherein the matrix comprises organic polymer.

7. The optical system of claim 1, wherein the matrix comprises poly(4-vinyl pyridine).

8. The optical system of claim 1, wherein the hydroxyazobenzene group is hydrogen bonded to the matrix.

9. The optical system of claims 1, wherein the hydroxyazobenzene group is part of a larger molecule or a polymer.

10. The optical system of claim 1, wherein the optically transparent matrix further comprises a second molecule containing a hydroxyazobenzene group embedded in the matrix.

11. The optical system of claim 1, wherein the optically transparent matrix further comprises a second isomerizing molecule or a thermochromic molecule embedded in the matrix.

12. The optical system of claim 11, wherein the optical system is arranged to measure temperature.

13. The optical system of claim 1, wherein the at least one light detector comprises one or more light intensity detector(s).

14. The optical system of claim 1, comprising a second light source as a measurement light.

15. The optical system of claim 1, wherein the isomerizing light source or the second light source is selected from a light-emitting diode and a laser.

16. The optical system of claim 15, wherein the isomerizing light source or the second light source provides light at a wavelength in the ultra violet range.

17. The optical system of claim 1, wherein the measurement control electronics are configured to obtain the quantity of hydrogen bonding gaseous molecules by using the dependency of the thermal cis-trans isomerization time constant on the quantity of the hydrogen bonding gas molecules based on one or more calibration curve(s).

18. The optical system of claim 1, comprising one or more optical fibers.

19. The optical system of claim 1, wherein the hydrogen bonding gaseous molecules are selected from at least one of the following: water, methanol, ethanol, and acetic acid.

20. The optical system of claim 1, wherein the optical system is arranged to measure humidity.

21. A method for measuring the quantity of hydrogen bonding gaseous molecules, the method comprising
providing an optically transparent matrix comprising a molecule containing a hydroxyazobenzene group embedded in the matrix or the optical system of claim 1;
illuminating the optically transparent matrix with isomerizing light capable of inducing trans-cis isomerization in the hydroxyazobenzene group;
measuring absorbance changes from the optically transparent matrix at a single or multiple wavelength(s) to obtain a thermal cis-trans isomerization time constant; and
obtaining the quantity of the hydrogen bonding gaseous molecules by using a dependency of the thermal cis-trans isomerization time constant on the quantity of the hydrogen bonding gaseous molecules.

22. The method of claim 21, wherein the molecule containing a hydroxyazobenzene group comprises the hydroxyazobenzene of Formula (I):

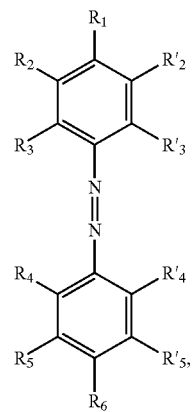

Formula (I)

wherein all $R_1$-$R'_6$ and $R'_2$-$R'_5$ are selected from —H, —OH, —(CH$_2$)$_x$CH$_3$, —O(CH$_2$)$_x$CH$_3$, —NO$_2$, —CN, —F, —CF$_3$ and —NH$_2$, wherein the hydroxyazobenzene of Formula (I) includes at least one —OH group.

23. The method of claim 21, wherein the molecule containing a hydroxyazobenzene group is 4-hydroxyazobenzene.

24. The method of claim 21, wherein the molecule containing a hydroxyazobenzene group is 4-octyl-4'-hydroxyazobenzene.

25. The method of claim 21, wherein the molecule containing a hydroxyazobenzene group is 4-ethyl-4'-hydroxyazobenzene.

26. The method of claim 21, wherein the matrix comprises organic polymer.

27. The method of claim 21, wherein the matrix comprises poly(4-vinyl pyridine).

28. The method of claim 21, wherein the hydroxyazobenzene group is hydrogen bonded to the matrix.

29. The method of claim 21, wherein the hydroxyazobenzene group is part of a larger molecule or a polymer.

30. The method of claim 21, wherein the optically transparent matrix further comprises a second molecule containing a hydroxyazobenzene group embedded in the matrix.

31. The method of claim 21, wherein the optically transparent matrix further comprises a second isomerizing molecule or a thermochromic molecule embedded in the matrix.

32. The method of claim 31, wherein the method is a method for measuring temperature.

33. The method of claim 21, wherein the hydrogen bonding gaseous molecules are being adsorbed into the optically transparent matrix.

34. The method of claim 21, wherein the hydrogen bonding gaseous molecules are selected from at least one of the following: water, methanol, ethanol, and acetic acid.

35. The method of claim 21, wherein the method is a method for measuring humidity.

\* \* \* \* \*